United States Patent
Terranova et al.

(10) Patent No.: US 6,179,883 B1
(45) Date of Patent: *Jan. 30, 2001

(54) 2-IMINO-2,3-DIHYDRO-1H-INDOLE DERIVATIVES FOR DYEING KERATIN FIBERS

(75) Inventors: Eric Terranova, Asnieres; Aziz Fadli, Le Blanc Mesnil; Alain Lagrange, Coupvray, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/916,663

(22) Filed: Aug. 22, 1997

(30) Foreign Application Priority Data

Aug. 23, 1996 (FR) .................................. 96 10412

(51) Int. Cl.$^7$ ............................ A61K 7/13; C07D 209/40
(52) U.S. Cl. .................... 8/423; 8/406; 8/574; 8/618; 548/483
(58) Field of Search ............................. 8/405, 406, 423, 8/618, 623, 624, 628, 574; 548/483

(56) References Cited

U.S. PATENT DOCUMENTS

| | | | |
|---|---|---|---|
| 3,000,899 | 9/1961 | Hoffmann et al. | 260/319 |
| 3,944,672 | 3/1976 | Steinman | 424/274 |
| 3,984,563 | 10/1976 | Winters | 424/274 |
| 4,620,850 | * 11/1986 | Bachmann et al. | 8/406 |
| 4,776,857 | * 10/1988 | Carroll et al. | 8/423 |
| 4,932,977 | * 6/1990 | Schultz | 8/423 |
| 5,053,053 | 10/1991 | De Labbey et al. | 8/423 |
| 5,112,360 | * 5/1992 | Garoche et al. | 8/406 |
| 5,131,911 | * 7/1992 | Lang et al. | 8/405 |
| 5,496,543 | 3/1996 | Lagrange et al. | 424/70.7 |
| 5,583,234 | 12/1996 | Lagrange et al. | 548/455 |
| 5,609,649 | 3/1997 | Junino et al. | 8/409 |

FOREIGN PATENT DOCUMENTS

| | | |
|---|---|---|
| 24 42 667 | 3/1975 | (DE) . |
| 0 376 776 | 7/1990 | (EP) . |
| 0 428 441 | 5/1991 | (EP) . |
| 2 008 797 | 1/1970 | (FR) . |
| 1 217 479 | 12/1970 | (GB) . |
| WO 92/17157 | 10/1992 | (WO) . |
| WO 93/13744 | 7/1993 | (WO) . |
| WO 93/13745 | 7/1993 | (WO) . |

OTHER PUBLICATIONS

Chemical Abtracts, vol. 79, No. 9, 1973 (abstract No. 53260x), Portnov et al.
Chemical Abstracts, vol. 78, No. 11, 1973 (abstract No. 71606y), Harmon et al.
Chemical Abstracts, vol. 87, No. 25, Dec. 19, 1977 (abstract No. 201378z), Sagitullin et al.
Chemical Abstracts, vol. 94, No. 13, Mar. 30, 1981 (abstract No. 103110f), Kost et al.
Chemical Abstracts, vol. 75, No. 23, Dec. 6, 1971 (abstract No. 140696e), Gorbunova et al.
Chemical Abstracts, vol. 74, No. 25, Jun. 21, 1971 (abstract No. 141438p), Itino et al.
Chemical Abstracts, vol. 73, No. 15, Oct. 12, 1970 (abstract No. 76975z), Sagitullin et al.
Chemical Abstracts, vol. 88, No. 17, Apr. 24, 1978 (abstract No. 121064z), Balli et al.
Chemical Abstracts, vol. 73, No. 9, Aug. 31, 1970 (abstract No. 45252g), Hino et al.
Chemical Abstracts, vol. 68, No. 23, Jun. 3, 1968 (abstract No. 105143f), Glushkov et al.
Chemical Abtracts, vol. 79, No. 5, Aug. 6, 1973 (abstract No. 31782s), Golubeva et al.
Chemical Abstracts, vol. 93, No. 11, Sep. 15, 1980 (abstract No. 114247m), Kost et al.

(List continued on next page.)

*Primary Examiner*—Caroline D. Liott
(74) *Attorney, Agent, or Firm*—Finnegan, Henderson, Farabow, Garrett & Dunner, L.L.P.

(57) ABSTRACT

Novel 2-imino-2,3-dihydro-1H-indole derivatives of formula (I) or (II) below:

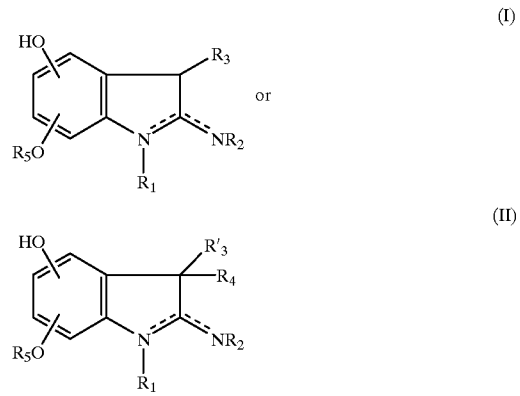

in which:

$R_1$, $R_2$ and $R_3$ denote hydrogen, alkyl, carboxyl, alkoxycarbonyl, monohydroxyalkyl, polyhydroxyalkyl, alkoxyalkyl, monoalkylaminoalkyl or dialkylaminoalkyl;

$R'_3$ and $R_4$ denote alkyl, carboxyl, alkoxycarbonyl, monohydroxyalkyl, polyhydroxyalkyl, alkoxyalkyl, monoalkylaminoalkyl or dialkylaminoalkyl;

$R_5$ denotes hydrogen, alkyl, monohydroxyalkyl, polyhydroxyalkyl, alkoxyalkyl, monoalkylaminoalkyl or dialkylaminoalkyl;

and the addition salts thereof with an acid, as well as their uses for dyeing keratin fibres.

21 Claims, No Drawings

OTHER PUBLICATIONS

Chemical Abstracts, vol. 90, No. 21, May 21, 1979 (abstract No. 168410r), Hiremath et al.
Chemical Abstracts, vol. 114, No. 13, Apr. 1, 1991 (abstract No. 121938t), Portner et al.
Chemical Abstracts, vol. 82, No. 23, Jun. 9, 1975 (abstract No. 156003g), Gilchrist et al.
Chemical Abstracts, vol. 80, No. 17, Apr. 29, 1974 (abstract No. 95788b), Abramenko.
Chemical Abstracts, vol. 108, No. 5, Feb. 1, 1988 (abstract No. 37569s), Portnov et al.
Chemical Abstracts, vol. 107, No. 10, Sep. 7, 1987 (abstract No. 88896h), Obtemperanskaya et al.
Chemical Abstracts, vol. 119, No. 3, Jul. 19, 1993 (abstract No. 27959g), Fernandez Garcia et al.
Chemical Abstracts, vol. 123, No. 1, Jul. 3, 1995 (abstract No. 252s), Fernandez Garcia et al.

* cited by examiner

2-IMINO-2,3-DIHYDRO-1H-INDOLE DERIVATIVES FOR DYEING KERATIN FIBRES

The present invention relates to novel 2-imino-2,3-dihydro-1H-indole derivatives, to a process for their preparation, to their use in dyeing keratin fibres such as the hair and to dyeing processes using them.

It has already been proposed in the past to dye the hair using, as couplers, certain monohydroxy-indoles or monoaminoindolines, in particular in French patent FR-A-2 008 797. U.S. Pat. No. 4,013,404 describes the use of mono- or diaminoindolines or monohydroxy-indolines as oxidation bases or as couplers in the oxidation dyeing of the hair.

Dyes of the indole family, in particular 5,6-dihydroxyindole, and their use for dyeing keratin fibres such as human hair are moreover known, in particular from French patents FR-A-1,133,594 and FR-A-1,166,172.

The inventors have discovered novel monoalkoxy, mono- or dihydroxy 2-imino-2,3-dihydro-1H-indole derivatives which can have noteworthy dyeing properties towards keratin fibres such as the hair. These compounds are readily oxidized in alkaline medium and may be used in hair dyeing possibly without using an oxidizing agent, which makes it possible to obtain a varied range of more or less intense shades.

The subject of the invention is novel 2-imino-2,3-dihydro-1H-indole derivatives as well as the addition salts thereof with an acid, of formula (I) or (II) which will be defined below.

Another subject of the invention is the use of these compounds in the dyeing of keratin fibres.

The subject of the invention is dye compositions intended for dyeing keratin fibres, and in particular human hair, containing at least one 2-imino-2,3-dihydro-1H-indole derivative of formula (I) or (II) defined below.

The subject of the invention is also dyeing processes using these compounds.

Other subjects of the invention will become apparent on reading the description and the examples which follow.

The 2-imino-2,3-dihydro-1H-indole derivatives in accordance with the invention correspond to formula (I) or (II) below:

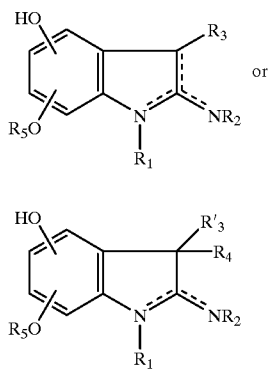

in which:
  R, $R_2$ and $R_3$, which may be identical or different, denote a hydrogen atom or a $C_1$–$C_4$ alkyl, carboxyl, alkoxy($C_1$–$C_4$)carbonyl, $C_1$–$C_4$ monohydroxyalkyl, $C_2$–$C_4$ polyhydroxyalkyl, ($C_1$–$C_4$)alkoxy($C_1C_4$)alkyl, mono($C_1$–$C_4$)alkylamino($C_1$–$C_4$)alkyl or di($C_1$–$C_4$)alkylamino($C_1$–$C_4$)alkyl radical;

$R'_3$ and $R_4$, which may be identical or different, denote a $C_1$–$C_4$ alkyl, carboxyl, ($C_1$–$C_4$)alkoxycarbonyl, $C_1$–$C_4$ monohydroxyalkyl, $C_2$–$C_4$ polyhydroxyalkyl, ($C_1$–$C_4$)alkoxy($C_1$–$C_4$)alkyl, mono($C_1$–$C_4$)alkylamino($C_1$–$C_4$)alkyl or di($C_1$–$C_4$)alkylamino($C_1$–$C_4$)alkyl radical;

$R_5$ denotes a hydrogen atom or a $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, mono($C_1$–$C_4$)alkylamino($C_1$–$C_4$)alkyl or di($C_1$–$C_4$)alkylamino($C_1$–$C_4$)alkyl radical;

it being possible for the said alkyl or alkoxy radicals to be linear or branched.

The addition salts with an acid of the compounds of formula (I) or (II) also constitute a subject of the invention, and may be chosen in particular from the hydrochlorides, hydrobromides, sulphates, tartrates, lactates and acetates.

Each of the formulae (I) or (II) defined above may give rise to several forms, in which the preponderance and/or stability of each form will depend on the nature of the various substituents $R_1$, $R_2$, $R_3$, $R'_3$ and $R_4$.

Formula (I) may give rise to the 3 forms below:

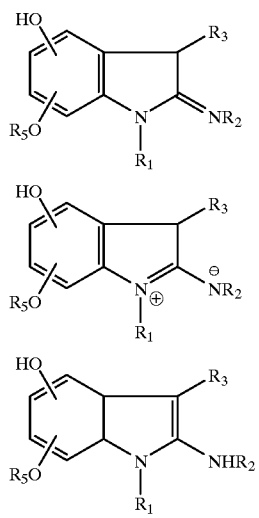

Formula (II) may give rise to the two forms below:

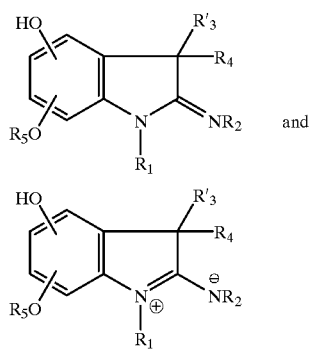

For the sake of clarity, all the 2-imino-2,3-dihydro-1H-indole derivatives will be defined hereinbelow by formulae (I) or (II) below:

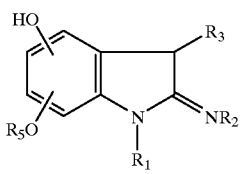

(I)

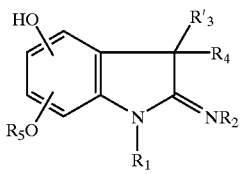

(II)

in which $R_1$, $R_2$, $R_3$, $R'_3$, $R_4$ and $R_5$ have the same meanings as those indicated above in the definitions of formulae (I) and (II).

Among the preferred compounds of formula (I) or (II) and the addition salts thereof with an acid, mention may be made more particularly of 5,6-dihydroxy-1,3-dihydroindol-2-ylideneamine and the addition salts thereof with an acid.

The specific compounds of formula (IA) or (IIA) below or the other forms thereof:

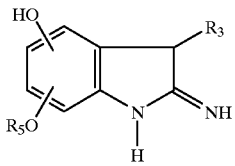

(IA)

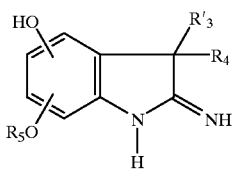

(IIA)

the radicals $R_3$, $R'_3$, $R_4$ and $R_5$ have the same meanings as those indicated above in the definitions of the formulae (I) and (II), may be obtained according to the process described in the RG Glushkov patent USSR Patent 179 320 (1965) and in the document Chem. Abstr 65, 2225(1966) and corresponding to schemes A and A' below:

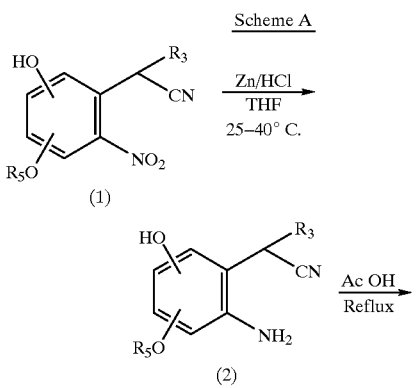

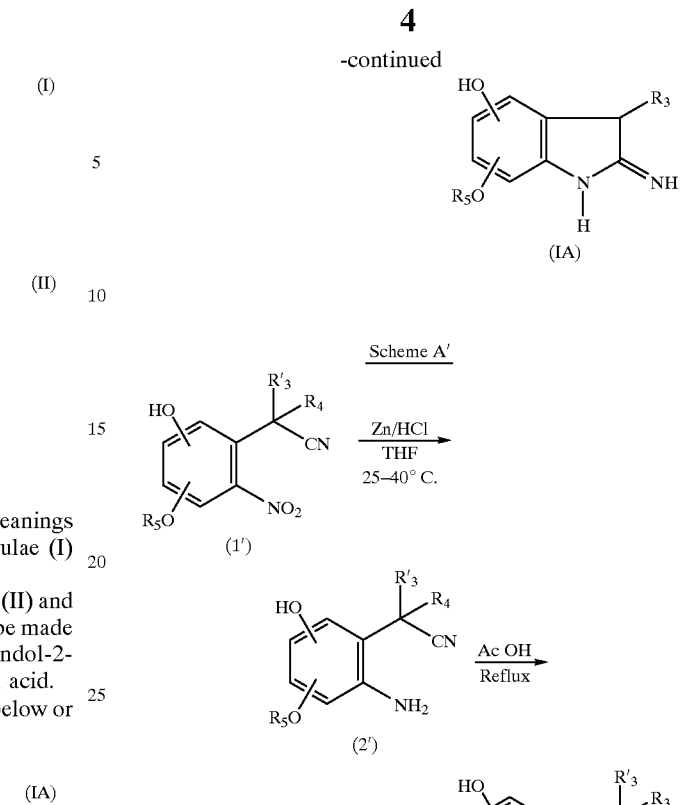

In Schemes A and A' defined above, the meanings of the radicals $R_3$, $R'_3$, $R_4$ and $R_5$ in formulae (1), (1'), (2) and (2') are identical to those indicated above in the formula (I) or (II).

This is a two-step process beginning with the starting compounds of formula (1) or (1') which have the structure of orthonitrophenylacetonitriles whose method of synthesis is as in the literature (M. Makosza, J. Winiarski, Acc. Chem. Res., 87, 1987, 282; M. Makosza, W. Danikiewicz, K. Wojciechowski; Liebigs Ann. Chem. 1988, 203).

The first step is preferably either a chemical reduction in the presence of an organic solvent using metals such as zinc or tin, or a selective hydrogenation using a catalyst such as palladium or platinum. The solvents used are preferably ethers and more particularly tetrahydrofuran (THF). The reaction temperature ranges preferably from 25° C. to the reflux temperature of the solvent and more particularly from 25 to 40° C.

The second step is preferably a cyclization reaction in acidic medium in the presence of an organic solvent. Acetic acid is preferably used. The reaction temperature is that of reflux of the solvent. The final product of formula (IA) or (IIA) is preferably isolated in the form of an addition salt with an acid. It is obtained by precipitation of the reaction medium in acidic medium. For example, in order to obtain a hydrochloride, a stream of HCl gas is passed through at the end of the reaction.

Specific compounds of formula (IB) or (IIB) corresponding respectively to formula (I) and to formula (II), in which $R_1$ is a hydrogen atom, and the specific compounds of formula (IC) or (IIC) corresponding respectively to formula (I) and to formula (II), in which $R_1$ and $R_2$ are both other than a hydrogen atom, may be obtained according to a preparation process, with reference to the literature, and corresponding to Schemes B and B' below:

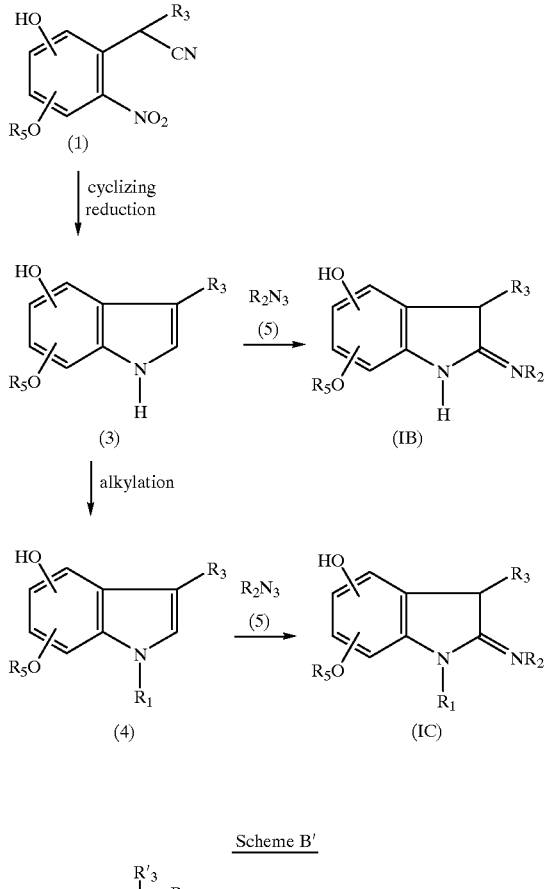

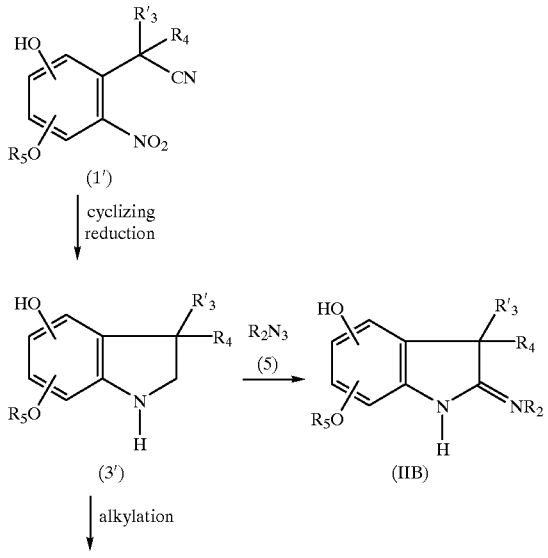

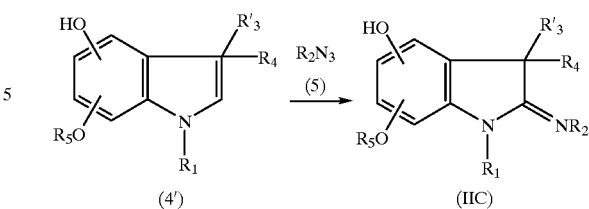

Compound (1) or (1') may be treated under cyclizing reduction conditions according to known methods such as, for example, that described by Makosza M. et al., in Liebigs Ann. Chem., 203, (1988) in order to lead respectively to the indole (3) or (3'). The indole (3) or (3') may be alkylated to lead respectively to the indole (4) or (4') according to standard methods as described, for example, in "Heterocyclic Compounds: Indoles" part 11 pp. 72–73, edited by N. J. Houlian, Wiley-Interscience.

Compounds (3) or (3') and (4) or (4') may react with an azide of structure (5) to lead respectively to the 2-iminoindolines of formula (IB) or (IIB) and (IC) or (IIC) according to a method which has already been described [Harmon R. E., et al., J. Org. Chem. 38(1), 11, (1973)].

The compounds of structures (IB) or (IIB) and (IC) or (IIC) may also be obtained by reaction of an amine $R_2NH_2$ respectively with a 2-indolinethione derivative of structure (6) or (6') and (7) or (7') as described by Hino T. et al. in Tetrahedron 27, 775, (1971) and represented in Schemes C and C' below:

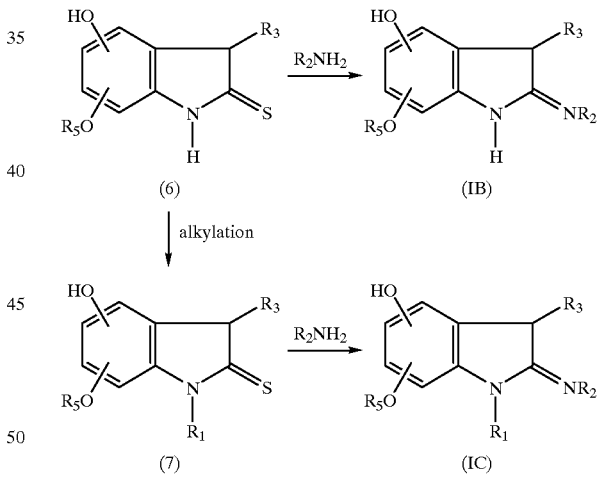

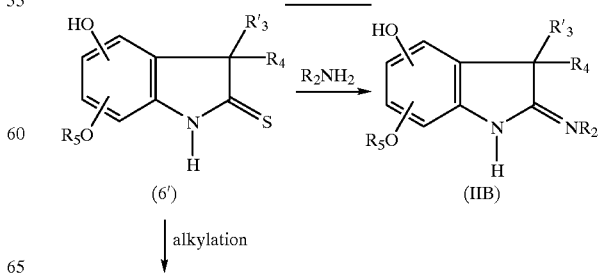

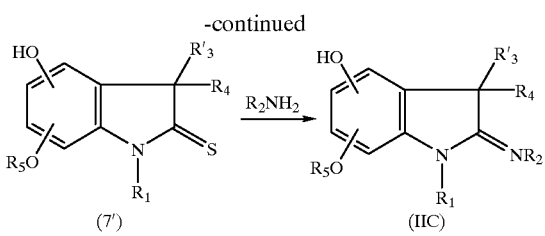

The 2-imino-2,3-dihydro-1H-indole derivatives of formula (I) or (II) defined above are generally used with the aid of compositions which constitute another subject of the invention.

The dye compositions intended to be used for dyeing keratin fibres, and in particular human keratin fibres such as the hair, in accordance with the invention are characterized in that they contain, preferably in a medium which is suitable for dyeing, at least one compound corresponding to formula (I) or (II) defined above.

The amount of compound of formula (I) or (II) used in the composition is generally present in proportions approximately ranging from 0.01 to 8% by weight relative to the total weight of the composition and preferably approximately 0.03 to 5% by weight.

These compositions may be in various forms in particular in the form of more or less thickened lotions, creams, mousses and gels, which may optionally be packaged in the form of aerosols.

The compositions may also constitute an element of a multi-component dyeing agent placed in a multi-compartment device or kit for dyeing.

The medium which is suitable for dyeing is preferably an aqueous medium which must be cosmetically acceptable when compositions are intended to be used for dyeing live human hair. This aqueous medium may comprise water or a water/solvent(s) mixture.

The pH of the compositions generally ranges from 3 to 12.

The solvents may be chosen from organic solvents and preferably from ethyl alcohol, propyl alcohol or isopropyl alcohol, tert-butyl alcohol, ethylene glycol, ethylene glycol monomethyl, monoethyl and monobutyl ethers, ethylene glycol monoethyl ether acetate, propylene glycol, propylene glycol and dipropylene glycol monomethyl ethers, and methyl lactate.

The solvents which are particularly preferred are ethyl alcohol, propylene glycol and ethylene glycol monobutyl ether.

The compounds in accordance with the invention have the advantage of being able to be used in an essentially aqueous medium.

It is also possible to use a medium comprising anhydrous solvents chosen from the solvents defined above. In this case, the composition is either mixed at the time of use with an aqueous medium or is applied to the keratin fibres which have been wettened beforehand with an aqueous composition.

In accordance with the invention, a medium containing less than 1% of water is called an anhydrous solvent medium.

When the medium which is suitable for dyeing comprises a water/solvent(s) mixture, the solvents are used in concentrations ranging from 0.5 to 75% by weight approximately, relative to the total weight of the composition, and preferably in proportions of less than 20% by weight approximately.

The compositions in accordance with the invention may contain adjuvants usually used for dyeing keratin fibres, and in particular cosmetically acceptable adjuvants when these compositions are applied for the dyeing of live human hair.

These compositions may contain in particular fatty amides in proportions ranging preferably from 0.05 to 10% by weight, anionic, cationic, nonionic or amphoteric surfactants or mixtures thereof, more preferably present in proportions ranging from 0.1 to 50% by weight, thickeners, fragrances, sequestering agents, film-forming agents, treatment agents, dispersing agents, conditioners, preserving agents, opacifiers and agents for swelling keratin fibres.

The thickeners are chosen from sodium alginate, gum arabic, guar gum, heterobiopoly-saccharides such as xanthan gum, scleroglucans, cellulose derivatives such as methylcellulose, hydroxyethylcellulose, hydroxypropylcellulose and sodium carboxymethylcellulose, and acrylic acid polymers which are preferably crosslinked.

Inorganic thickeners such as bentonite may also be used.

These thickeners are used alone or as a mixture and are preferably present in proportions ranging from 0.1 to 5% by weight relative to the total weight of the composition and advantageously from 0.5 to 3% by weight.

The basifying agents which may be used in the compositions may be, in particular, amines such as alkanolamines or alkylamines, and ammonium or alkali metal hydroxides or carbonates.

The acidifying agents which may be used in these compositions may be chosen from lactic acid, acetic acid, tartaric acid, phosphoric acid, hydrochloric acid and citric acid.

It is, of course, possible to use any other acceptable basifying or acidifying agents, in particular in the case of cosmetic dyeing of the hair.

When the compositions are used in the form of a mousse, they may be packaged under pressure and in an aerosol device in the presence of a propellant and at least one foam generator.

The foam generators may be anionic, cationic, nonionic or amphoteric foaming polymers or mixtures thereof or surfactants of the type defined above.

The process for dyeing keratin fibres, in particular human keratin fibres, which constitutes another subject of the invention is essentially characterized in that it comprises the steps of applying to these fibres a composition (A) defined above, of keeping the composition in contact with the fibres for a period which is sufficient to develop the coloration, either in air or using an oxidizing system, of rinsing and optionally of washing the fibres thus dyed.

According to a first embodiment of the invention, the fibres may be dyed without addition of an external oxidizing agent, solely by contact with the air.

According to another embodiment, the colour is developed using a chemical oxidizing system chosen from:
(i) iodide ions and hydrogen peroxide, the composition (A) containing the compound of formula (I) or (II) also comprising, in this case, either at least one iodide ion or hydrogen peroxide, and application of the composition (A) is preceded or followed by the application of a composition (B) which contains, in a medium which is suitable for dyeing, either:
  (a) hydrogen peroxide at a pH ranging from 2 to 12 and preferably from 2 to 7, when the composition (A) contains at least one iodide ion, or:
  (b) at least one iodide ion at a pH ranging from 3 to 11 when the composition (A) contains hydrogen peroxide;
(ii) nitrites, application of the composition (A) containing the compound of formula (I) or (II) being followed by the application of an aqueous composition (B) having an acidic pH, the composition (A) or the composition (B) containing at least one nitrite;

(iii) oxidizing agents chosen from hydrogen peroxide, periodic acid and its water-soluble salts, sodium hypochlorite, chloramine T, chloramine B, potassium ferricyanide, silver oxide, Fenton's reagent, lead (IV) oxide, caesium sulphate, ammonium persulphate and alkali metal chlorites; these oxidizing agents being present in composition (A) containing the compound of formula (I) or (II) or applied, simultaneously or sequentially, by means of a composition (B) containing them in a medium which is suitable for dyeing;

(iv) anions of a metal chosen from the permanganates or dichromates, these anions being applied by means of an aqueous composition (B) containing them, at a pH ranging from 2 to 10, before the composition (A) is applied;

(v) salts of metals from groups 3 to 8 of the Periodic Table, these metal salts being applied by means of a composition (B) containing them in a medium which is suitable for dyeing, the composition (B) being applied before or after the composition (A) is applied;

(vi) rare-earth metal salts, these rare-earth metal salts being applied by means of a composition (B) containing them in a medium which is suitable for dyeing, the composition (B) being applied before or after the composition (A) containing the compound of formula (I) or (II) is applied;

(vii) a quinone derivative chosen from ortho- or para-benzoquinones, monoimine or diimine ortho- or para-benzoquinones, 1,2- or 1,4-naphthoquinones, sulphonimide ortho- or para-benzoquinones, α,ω-alkylenebis-1,4-benzoquinones or monoimine or diimine 1,2- or 1,4-naphthoquinones, these quinone derivatives being applied by means of a composition (B) containing them in a medium which is suitable for dyeing, the compound of formula (I) or (II) and the quinone derivatives being chosen such that the redox potential difference ΔE between the redox potential Ei of the compound of formula (I) or (II) determined at pH 7 in phosphate medium on a glass carbon electrode by voltammetry and the redox potential Eq of the quinone derivative determined at pH 7 in phosphate medium by polarography on a mercury electrode relative to the saturated calomel electrode, is such that:

$$\Delta E = Ei - Eq \leq 320 \text{ millivolts};$$

the composition (B) being applied before or after the composition (A) containing the compound of formula (I) or (II) is applied.

According to a preferred form of the invention, the application of the compositions (A) and (B) is separated by a step of rinsing with water.

As quinone derivatives which may be used in this process, mention may be made of:
1,4-benzoquinone,
2-methoxy-1,4-benzoquinone,
2-methyl-1,4-benzoquinone,
2,6-dimethyl-1,4-benzoquinone,
2,3,5-trichloro-6-methyl-1,4-benzoquinone,
2-acetylamino-1,4-benzoquinone,
2-acetylamino-3,5-dimethyl-1,4-benzoquinone,
2,6-dimethyl-5-acetylamino-1,4-benzoquinone,
2-chloro-1,4-benzoquinone,
tetrachloro-1,2-benzoquinone,
2,3-dimethoxy-1,4-benzoquinone,
2-β-carboxyethoxy-1,4-benzoquinone,
2-methoxymethyl-1,4-benzoquinone,
2-β-hydroxyethyl-1,4-benzoquinone,
2-β-hydroxyethylthio-1,4-benzoquinone,
2,5-bis-β-hydroxyethylthio-1,4-benzoquinone,
2-β-dihydroxypropylthio-1,4-benzoquinone,
2-β-carboxyethylthio-1,4-benzoquinone,
2-carboxymethyl-1,4-benzoquinone,
2-β-hydroxyethylthio-6-methyl-1,4-benzoquinone,
2-methoxycarbonyl-3-methoxy-1,4-benzoquinone,
2-methoxycarbonyl-1,4-benzoquinone,
2-methylthio-1,4-benzoquinone,
2-dimethylamino-1,4-benzoquinone,
2-acetylamino-5-methoxy-1,4-benzoquinone,
2-(β-hydroxyethylthio)methyl-1,4-benzoquinone,
2-(methylthio)methyl-1,4-benzoquinone,
4,5-dimethoxy-1,2-benzoquinone,
4-methyl-5-chloro-1,2-benzoquinone,
4,5-dimethyl-1,2-benzoquinone,
2,3-dimethyl-1,4-benzoquinone,
2-β-hydroxyethoxy-1,4-benzoquinone,
N-methylsuphonyl-1,4-benzoquinone monoimine,
N-phenylsulphonyl-1,4-benzoquinone monoimine,
1,4-naphthoquinone,
1,2-naphthoquinone,
1,2-naphthoquinone-4-sulphonic acid,
2,3-dichloro-1,4-naphthoquinone and
N-2,6-dichloro-1,4-benzoquinoneimine.

According to a first variant of the dyeing process using oxidizing systems, a composition (A) containing, in a medium which is suitable for dyeing, at least one compound of formula (I) or (II) in combination with iodide ions is applied to the keratin substances, application of the composition (A) being preceded or followed by the application of a composition (B) which contains hydrogen peroxide in a medium which is suitable for dyeing.

This process may also be carried out by applying to the keratin fibres at least one composition (A) containing, in a medium which is suitable for dyeing, the compound of formula (I) or (II) in combination with hydrogen peroxide, preferably having a pH ranging from 2 to 7 and more preferably from 3.5 to 7, application of the composition (A) being preceded or followed by the application of a composition (B) which contains iodide ions in a medium which is suitable for dyeing.

The iodide ion in this variant of the process is preferably chosen from alkali-metal, alkaline-earth metal or ammonium iodides. The iodide is more particularly potassium iodide.

The iodide ions are present in compositions (A) or (B) in proportions ranging generally from 0.007 to 4% by weight, expressed as ions I, and preferably from 0.08 to 1.5% by weight relative to the total weight of the composition (A) or (B).

According to a second variant, this process may be carried out using a nitrite as oxidizing agent to develop the colour. The nitrites which may be used more particularly in accordance with the invention are:

alkali-metal, alkaline-earth metal or ammonium nitrites or any other cosmetically acceptable cation when it is used to dye live human hair;

organic nitrite derivatives such as, for example, amyl nitrite;

nitrite vectors, that is to say compounds which form nitrites of the type defined above by transformation.

The nitrites particularly preferred are sodium, potassium and ammonium nitrites.

This variant of the process is carried out by applying to the keratin substances composition (A) based on the compound of formula (I) or (II) defined above, followed by an aqueous acidic composition (B), composition (A) or (B) containing at least one nitrite.

The nitrites are generally used in proportions from 0.02 to 1 mol/liter.

According to a third variant of this process, the oxidizing agents are chosen from hydrogen peroxide, chloramine B, periodic acid and its water-soluble salts, sodium hypochlorite, potassium ferricyanide, silver oxide, Fenton's reagent, lead (IV) oxide, caesium sulphate and ammonium persulphate. These agents are preferably applied to the fibres by means of a composition (B) and after the composition (A) has been applied.

These oxidizing agents are present in proportions which are sufficient to develop a colour and preferably in proportions from 0.004 mol to 0.04 mol per 100 g of composition.

According to a fourth variant of this process, in a first stage, a composition (B) is applied to the keratin substances, this composition containing, in a medium which is suitable for dyeing, at a pH preferably ranging from 2 to 10, an anion of a metal having good affinity for keratin and having a redox potential greater than that of the compounds of formula (I) or (II). This anion is preferably chosen from permanganates or dichromates and more particularly potassium permanganate and sodium dichromate.

These metal anions are generally used at anion molalities of greater than $10^{-3}$ mol/1000 g and preferably up to 1 mol/1000 g.

In a second stage, a composition (A) is applied which contains, in a medium which is suitable for dyeing, at a pH ranging from 4 to 10, at least one compound corresponding to formula (I) or (II) defined above.

The compositions containing the anions should not contain organic agents which have a reducing effect on the anions.

According to a fifth variant of the invention, oxidation catalysts chosen from metal salts such as manganese salts, cobalt chloride, ferric chloride, cupric chloride and ammoniacal silver nitrate are used.

The preferred salts are copper salts. These salts are used in proportions ranging from 0.01 to 2%, expressed as metal ions, relative to the total weight of the composition used and containing these salts.

According to this variant, the keratin fibres, in particular the hair, are placed in contact with a composition (B) containing, in a medium which is suitable for dyeing, the metal salt, before or after the composition (A) containing the compound of formula (I) or (II) has been applied, and rinsing is preferably carried out between the two steps.

The preferred embodiment comprises the steps of applying a cupric salt in a first stage and the composition (A) containing the compound of formula (I) or (II) in a second stage.

This dyeing operation may be followed, after rinsing, by applying a hydrogen peroxide solution in order optionally to lighten the colour obtained.

According to a sixth variant, rare-earth metal salts are used. The rare-earth metal salts which may be used in accordance with the invention are chosen from lanthanides and in particular cerium $Ce^{3+}$ and $Ce^{4+}$, lanthanum $La^{3+}$, europium $Eu^{2+}$ and $Eu^{3+}$, gadolinium $Gd^{3+}$, ytterbium $Yb^{2+}$ and $Yb^{3+}$ and dysprosium $Dy^{3+}$ salts. The preferred salts are, in particular, the sulphates, chlorides or nitrates.

These rare-earth metal salts are present in proportions ranging from 0.1 to 8% by weight relative to the total weight of the composition.

The cerium $Ce^{3+}$ and $Ce^{4+}$ salts in the form of sulphates and chlorides are preferably used.

According to a seventh variant, the composition containing the quinone derivative is applied before or after the composition (A) containing the compound of formula (I) or (II).

1,4-Benzoquinone and 2-β-hydroxyethylthio-1,4-benzoquinone may be mentioned as preferred quinone derivatives.

The concentration of quinone derivatives ranges preferably from 0.005 to 1 mol/liter in the composition (B). The pH of the composition (B) preferably ranges from 2 to 10 and is more preferably less than 7.

When compositions based on hydrogen peroxide are used in the various processes described above, the hydrogen peroxide content ranges generally from 1 to 40 volumes and preferably from 2 to 10 volumes and more particularly from 3 to 10 volumes.

The subject of the invention is also a multi-component agent for dyeing keratin fibres, and in particular human keratin fibres, which is intended to be used in particular to carry out the dyeing process defined above and using an oxidizing system. In this case, the dyeing agent comprises at least two components, the first of which contains the composition (A) defined above and containing the compound of formula (I) or (II), and the other component containing one of the compositions (B) also defined above.

The respective components (A) and (B) are chosen according to the different variants of the process which have been outlined above.

The subject of the invention is also a multi-compartment device or "dyeing kit" or "dyeing equipment" containing all the components intended to be applied in a given dyeing operation on keratin fibres by single or successive application with or without premixing, as mentioned above.

Such devices are known per se and may include a first compartment containing the composition (A) which contains the compound of formula (I) or (II) in a medium which is suitable for dyeing, and, in a second compartment, a composition (B) of the type defined above and containing the oxidizing agent.

The multi-compartment devices which may be used in accordance with the invention may be equipped with means for mixing at the time of use, and their content may be packaged under inert atmosphere.

When the medium containing the compound of formula (I) or (II) is anhydrous, a third compartment may be provided, this compartment containing an aqueous medium which is suitable for dyeing and intended to be mixed, just before use, with the composition of the first compartment.

The compound of formula (I) or (II), the compositions and the process in accordance with the invention may be used to dye natural or already dyed hair which may or may not have been permanent-waved and may or may not have been straightened, or hair which has been strongly or lightly bleached and possibly permanent-waved.

It is also possible to use them to dye fur or wool.

The examples which follow are intended to illustrate the invention without, however, being limiting in nature.

EXAMPLES

Example 1

Preparation of 5,6-dihydroxy-1,3-dihydroindol-2-ylideneamine hydrochloride 15.3 g of (4,5-dihydroxy-2-nitrophenyl)-acetonitrile were dissolved in a 70 ml/54 ml THF/37% HCl mixture in a 250 ml three-necked round-bottomed flask fitted with a condenser, a thermometer and a solids-addition funnel. 35 g of zinc powder were then added portionwise while maintaining the temperature below 60° C. After complete addition of the zinc, the reaction medium was allowed to cool to room temperature and was then filtered through Celite. The filtrate, cooled to ice-bath temperature, was saturated with hydrogen chloride gas. The 5,6-dihydroxy-1,3-dihydroindol-2-ylideneamine hydrochloride precipitated out. It was filtered off, washed with petroleum ether and dried under vacuum over phosphorus pentoxide and potassium hydroxide at 40° C. (Yield=90%). $^1$H and $^{13}$C NMR in accordance with the structure.

$^1$H NMR (DMSO-$d_6$; 400 MHz)

| δ (ppm) | multiplicity | integration |
|---|---|---|
| 3.97 | s | 2 |
| 6.67 | s | 1 |
| 6.80 | s | 1 |
| 8.00–9.00 | m | 2 |
| 9.42–9.66 | 2 s | 2 |
| 11.69 | s | 1 |

FORMULATION EXAMPLES AND DYEING PROCESSES

Example 1

Dye composition A below was prepared (content in grams):

| 5,6-dihydroxy-1,3-dihydroindol-2-ylideneamine Hcl | 1 g |
|---|---|
| 20% aqueous ammonia | 2 g |
| demineralized water qs | 100 g |

Dyeing Process 1 (oxidation with atmospheric oxygen)
Composition A was applied for 30 minutes to locks of permanent-waved or non-permanent-waved, natural grey hair containing 90% white hairs at a rate of 28 g per 3 g of hair. After rinsing, washing with a standard shampoo and drying, the locks were dyed in the shades shown in Table I below:

Dyeing Process 2 (oxidation with aqueous hydrogen peroxide solution)
Composition A was mixed, at the time of use, with an equal weight of 20-volumes aqueous hydrogen peroxide solution (6% by weight).
The mixture obtained was applied for 30 minutes to locks of permanent-waved or non-permanent-waved natural grey hair containing 90% white hairs at a rate of 28 g per 3 g of hair. After rinsing, washing with a standard shampoo and drying, the locks were dyed in the shades shown in Table I below:

TABLE 1

| Dyeing process | 1 | 2 |
|---|---|---|
| Shade obtained on natural grey hair containing 90% white hairs | Intense matt-grey-dark blonde | Very light blonde-beige |

TABLE 1-continued

| Dyeing process | 1 | 2 |
|---|---|---|
| Shade obtained on permanent-waved grey hair containing 90% white hairs | Matt dark chestnut-grey | Matt golden dark blonde |

Strong coloration having good light-fastness is obtained.

We claim:
1. 5,6-Dihydroxy-1,3-dihydroindol-2-ylideneamine, an acid addition salt thereof, or a mixture thereof.
2. A process for dyeing keratin fibers comprising:
   applying at least one dye composition to said fibers, wherein said at least one dye composition comprises at least one 2-imino-2,3-dihydro-1H-indole compound chosen from compounds of formula (I), compounds of formula (II), and acid addition salts thereof,

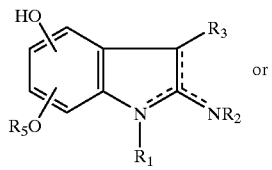

(I)

or

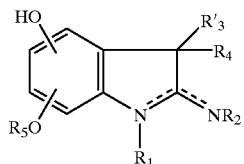

(II)

wherein:
   $R_1$, $R_2$ and $R_3$, which may be identical or different, are chosen from a hydrogen atom and $C_1$–$C_4$ alkyl, carboxyl, ($C_1$–$C_1$)alkoxycarbonyl, $C_1$–$C_4$ monohydroxyalkyl, $C_2$–$C_4$ polyhydroxyalkyl, ($C_1$–$C_4$)alkoxy($C_1$–$C_4$)alkyl, mono($C_1$–$C_1$)alkylamino($C_1$–$C_4$)alkyl and di($C_1$–$C_4$)alkylamino($C_1$–$C_4$)alkyl radicals;
   $R'_3$ and $R_4$, which may be identical or different, are chosen from $C_1$–$C_4$ alkyl, carboxyl, ($C_1$–$C_4$)alkoxycarbonyl, $C_1$–$C_4$ monohydroxyalkyl, $C_2$–$C_4$ polyhydroxyalkyl, ($C_1$–$C_4$)alkoxy($C_1$–$C_4$)alkyl, mono($C_1$–$C_4$)alkylamino-($C_1$–$C_4$)alkyl and di($C_1$–$C_4$)alkylamino ($C_1$–$C_4$)alkyl radicals;
   $R_5$ is chosen from a hydrogen atom and $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, mono($C_1$–$C_4$)alkylamino ($C_1$–$C_4$)alkyl and di($C_1$–$C_4$)alkylamino($C_1$–$C_4$)alkyl radicals;
wherein said alkyl or alkoxy radicals may be linear or branched, or a mixture thereof,
   keeping said at least one dye composition in contact with said fibers in the presence of an oxidizing system for a period which is sufficient to develop a coloration, and
   rinsing said keratin fibers,
   wherein said oxidizing system is selected from the group consisting of:
   (i)iodide ions and hydrogen peroxide, said dye composition further comprising either at least one iodide ion or hydrogen peroxide, application of said dye composition being preceded or followed by the application of a second composition comprising, in a medium which is suitable for dyeing, whichever of said at least one iodide ion or hydrogen peroxide that is not contained in said dye composition, wherein the pH of said composition containing hydrogen peroxide ranges from 2 to 12, and further wherein the pH of said other composition containing at least one iodine ion ranges from 3 to 11;

(ii) nitrites, application of said dye composition being followed by the application of an aqueous composition having an acidic pH, at least one of said dye composition and said aqueous composition containing at least one nitrite;

(iii) oxidizing agents, wherein said oxidizing agents are chosen from hydrogen peroxide, periodic acid and its water-soluble salts, sodium hypochlorite, (N-chloro-p-toluenesulfonamido)sodium, (N-chlorobenzenesulfonamido)sodium, potassium ferricyanide, silver oxide, Fenton's reagent, lead (IV) oxide, caesium sulphate, ammonium persulphate and alkali metal chlorites, said oxidizing agents being present in said dye composition or applied, simultaneously or sequentially, by means of a second composition containing them in a medium which is suitable for dyeing;

(iv) anions of a metal, wherein said anions are permanganate or dichromate, and said anions being applied by means of an aqueous composition containing them, at a pH ranging from 2 to 10, before said dye composition is applied;

(v) salts of metals from groups 3 to 8 of the Periodic Table, said salts being applied by means of a composition containing them in a medium which is suitable for dyeing, said composition containing said salts being applied before or after said dye composition is applied;

(vi) rare-earth metal salts, said rare-earth metal salts being applied by means of a composition containing them in a medium which is suitable for dyeing, said composition containing said rare-earth metal salts being applied before or after said dye composition is applied; and (vii) quinone derivatives, wherein said quinone derivatives are chosen from ortho- and para-benzoquinones, monoimine and diimine ortho- and para-benzoquinones, 1,2- and 1,4-naphthoquinones, sulphonimide ortho- and para-benzoquinones, $\alpha,\omega$-alkylenebis-1,4-benzoquinones, monoimine 1,2- and 1,4-naphthoquinones, and diimine 1,2- or 1,4-naphthoquinones, said quinone derivatives being applied by means of a composition containing them in a medium which is suitable for dyeing, the compound of formula (I) or (II) and said quinone derivatives being selected such that the redox potential difference $\Delta E$ between the redox potential $Ei$ of the compound of formula (I) or (II) determined at pH 7 in phosphate medium on a glass carbon electrode by voltammetry and the redox potential $Eq$ of the quinone derivatives determined at pH 7 in phosphate medium by polarography on a mercury electrode relative to the saturated calomel electrode, is such that:

$\Delta E = Ei - Eq \leq 320$ millivolts;

said composition containing said quinone derivatives being applied before or after said dye composition is applied.

3. A process according to claim 2, wherein said oxidizing system comprises iodide ions and hydrogen peroxide, and further wherein the composition containing hydrogen peroxide has a pH ranging from 2 to 7.

4. A process according to claim 2, wherein said oxidizing system comprises iodide ions and hydrogen peroxide, and further wherein said at least one iodide ion is present in proportions ranging from 0.007 to 4% by weight, expressed as ions $I^-$, relative to the total weight of the composition containing it.

5. A process according to claim 2, wherein said oxidizing system comprises anions of a metal, said metal being a permanganate or a dichromate, and further wherein said dye composition has a pH ranging from 4 to 10.

6. A process according to claim 5, wherein said permanganate or dichromate metal is present in an anion molality of greater than $10^{-3}$ mol/1000 g, and further wherein said composition contains no organic agents having a reducing effect on the anions.

7. A process according to claim 6, wherein said anion modalities range up to 1 mol/1000 g.

8. A process according to claim 2, wherein said salts of metals are chosen from manganese, cobalt, iron, copper and silver salts.

9. A process according to claim 8, wherein said salts of metals are included in proportions ranging from 0.01 to 2% by weight, expressed as metal ions, relative to the total weight of the composition containing them.

10. A process according to claim 2, wherein said rare-earth metal salts are chosen from cerium salts, lanthanum salts, europium salts, gadolinium salts, ytterbium salts, and dysprosium salts.

11. A process according to claim 10, wherein said rare-earth metal salts are present in proportions ranging from 0.1 to 8% by weight relative to the total weight of the composition containing them.

12. A process according to claim 2, wherein said quinone derivatives are chosen from 1,4-benzoquinone and 2-$\beta$-hydroxyethylthio-1,4-benzoquinone.

13. A process according to claim 12, wherein said quinone derivatives are present in said oxidizing system in proportions ranging from 0.005 to 1 mol/liter.

14. A process according to claim 2, wherein said oxidizing system comprises a composition containing hydrogen peroxide.

15. A process according to claim 14, wherein the hydrogen peroxide content in said composition containing hydrogen peroxide ranges from 1 to 40 volumes.

16. A process according to claim 15, wherein said hydrogen peroxide content ranges from 2 to 10 volumes.

17. A multi-component agent for dyeing keratin fibres comprising:

a first component containing at least one dye composition for the dyeing of keratin fibres, said at least one dye composition comprising at least one 2-Imino-2,3-dihydro-1H-indole derivative having the formula (I) or (II) below or an acid addition salt thereof:

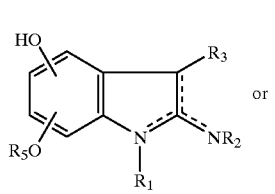

(I)

or

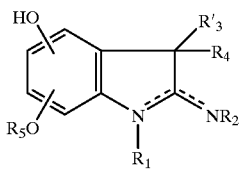

wherein:
- R₁, R₂ and R₃, which may be identical or different, are chosen from a hydrogen atom and $C_1$–$C_4$ alkyl, carboxyl, $(C_1$–$C_4)$alkoxycarbonyl, $C_1$–$C_4$ monohydroxyalkyl, $C_2$–$C_4$ polyhydroxyalkyl, $(C_1$–$C_4)$ alkoxy$(C_1$–$C_4)$alkyl, mono$(C_1$–$C_4)$alkylamino$(C_1$–$C_4)$ alkyl and di$(C_1$–$C_4)$alkylamino$(C_1$–$C_4)$alkyl radicals;
- R'₃ and R₄, which may be identical or different, are chosen from $C_1$–$C_4$ alkyl, carboxyl, $(C_1$–$C_4)$alkoxycarbonyl, $C_1$–$C_4$ monohydroxyalkyl, $C_2$–$C_4$ polyhydroxyalkyl, $(C_1$–$C_4)$alkoxy$(C_1$–$C_4)$alkyl, mono$(C_1$–$C_4)$ alkylamino-$(C_1$–$C_4)$alkyl and di$(C_1$–$C_4)$alkylamino $(C_1$–$C_4)$alkyl radicals;
- R₅ is chosen from a hydrogen atom and $C_1$–$C_4$ alkyl, $C_1$–$C_4$ monohydroxyalkyl, $C_2$–$C_4$ polyhydroxyalkyl, $(C_1$–$C_4)$alkoxy$(C_1$–$C_4)$alkyl, mono$(C_1$–$C_4)$ alkylamino-$(C_1$–$C_4)$alkyl and di$(C_1$–$C_4)$alkylamino $(C_1$–$C_4)$alkyl radicals;

wherein said alkyl or alkoxy radicals may be linear or branched, or a mixture thereof; and a second component containing an oxidizing system comprising:
(i) iodide ions and hydrogen peroxide,
wherein said first component containing at least one dye composition further comprises either at least one iodide ion or hydrogen peroxide and said second component comprises, in a medium which is suitable for dyeing, hydrogen peroxide at a pH of from 2 to 12 when said first component contains at least one iodide ion or at least one iodide ion at a pH of from 3 to 11 when said first component contains hydrogen peroxide;
(ii) an aqueous composition having an acidic pH which is applied following the application of said first component, wherein at least one of said dye composition and said aqueous composition contains at least one nitrite;
(iii) an oxidizing agent in a medium suitable for dyeing, wherein said oxidizing agent is chosen from hydrogen peroxide, periodic acid and its water-soluble salts, sodium hypochlorite, N-chloro toluylsulfonamide, potassium ferricyanide, silver oxide, Fenton's reagent, lead (IV) oxide, caesium sulphate, ammonium persulphate and an alkali metal chlorite;
(iv) an aqueous composition comprising anions of a metal chosen from permanganate and dichromate, wherein said aqueous composition has a pH of from 2 to 10;
(v) salts of metals from groups 3 to 8 of the Periodic Table in a medium suitable for dyeing;
(vi) rare-earth metal salts in a medium suitable for dyeing; or
(vii) quinone derivatives, wherein said quinone derivatives are chosen from ortho- and para-benzoquinones, monoimine and diimine ortho- and para-benzoquinones, 1,2- and 1,4-naphthoquinones, sulphonimide ortho- and para-benzoquinones, α,ω-alkylenebis-1,4-benzoquinones, monoimine 1,2- and 1,4-naphthoquinones, and diimine 1,2- or 1,4-naphthoquinones, said quinone derivative being selected such that the redox potential difference ΔE between the redox potential Ei of the compound of formula (I) or (II) determined at pH 7 in phosphate medium on a glass carbon electrode by voltammetry and the redox potential Eq of the quinone derivative determined at pH 7 in phosphate medium by polarography on a mercury electrode relative to the saturated calomel electrode, is such that: $\Delta E = Ei - Eq \leq 320$ millivolts.

18. A multi-component agent according to claim 17, wherein said keratin fibres are human keratin fibres.

19. A multi-compartment device or dyeing kit comprising at least two components, said first component according to claim 17 being present in at least one compartment and said second component according to claim 17 being present in at least one other compartment.

20. A process according to claim 2, wherein said nitrites are nitrites of alkali metals, of alkaline-earth metals, of ammonium, or of any other cosmetically acceptable cation, are organic nitrite derivatives, or are nitrite vectors which generate any of said nitrites.

21. A process according to claim 20, wherein said nitrites are present in said oxidizing system in proportions ranging from 0.02 to 1 mol/liter.

\* \* \* \* \*

UNITED STATES PATENT AND TRADEMARK OFFICE
CERTIFICATE OF CORRECTION

PATENT NO.   : 6,179,883 B1                                               Page 1 of 1
DATED        : January 30, 2001
INVENTOR(S)  : Eric Terranova et al.

It is certified that error appears in the above-identified patent and that said Letters Patent is hereby corrected as shown below:

<u>Column 14, claim 1,</u>
Line 40, "$(C_1-C_1)$alkoxycarbonyl" should read -- $(C_1-C_4)$alkoxy-carbonyl --

Signed and Sealed this

Twenty-ninth Day of January, 2002

Attest:

Attesting Officer

JAMES E. ROGAN
*Director of the United States Patent and Trademark Office*